United States Patent
Dove et al.

(10) Patent No.: US 11,678,822 B2
(45) Date of Patent: Jun. 20, 2023

(54) SENSOR JOINT WRAPPING IN A MEDICAL SENSOR

(71) Applicant: Covidien LP, Mansfield, MA (US)

(72) Inventors: Jacob Dove, Lafayette, CO (US);
Sarah L. Hayman, Boulder, CO (US);
Derek L. Moody, Longmont, CO (US);
Linden A. Reustle, Milliken, CO (US);
Shai Fleischer, Modiin (IL)

(73) Assignee: Covidien LP, Mansfield, MA (US)

( * ) Notice: Subject to any disclaimer, the term of this patent is extended or adjusted under 35 U.S.C. 154(b) by 268 days.

(21) Appl. No.: 16/904,626

(22) Filed: Jun. 18, 2020

(65) Prior Publication Data

US 2021/0393177 A1 Dec. 23, 2021

(51) Int. Cl.
*A61B 5/1455* (2006.01)
*A61B 5/00* (2006.01)

(52) U.S. Cl.
CPC ........ *A61B 5/14552* (2013.01); *A61B 5/7435* (2013.01); *A61B 2562/02* (2013.01); *A61B 2562/0233* (2013.01); *A61B 2562/12* (2013.01); *A61B 2562/166* (2013.01)

(58) Field of Classification Search
CPC .............. A61B 5/1455; A61B 5/14552; A61B 2562/0233; A61B 2562/166; A61B 2562/12
See application file for complete search history.

(56) References Cited

U.S. PATENT DOCUMENTS

| | | | |
|---|---|---|---|
| 4,974,591 A | 12/1990 | Awazu et al. | |
| 6,112,107 A * | 8/2000 | Hannula | A61B 5/14552 600/323 |
| 7,359,742 B2 * | 4/2008 | Maser | A61B 5/14552 600/344 |
| 8,070,508 B2 * | 12/2011 | Flagler | A61B 5/0002 439/470 |
| 8,251,739 B2 | 8/2012 | Flagler | |
| 8,315,685 B2 | 11/2012 | Arizaga Ballesteros | |
| 8,452,366 B2 | 5/2013 | Gilland | |
| 8,543,181 B2 * | 9/2013 | Karma | A61B 5/6826 600/344 |
| D862,709 S | 10/2019 | Besko et al. | |
| 2006/0241363 A1 | 10/2006 | Al-Ali et al. | |
| 2019/0058281 A1 | 2/2019 | Al-Ali et al. | |

FOREIGN PATENT DOCUMENTS

CN 108888275 A 11/2018

OTHER PUBLICATIONS

International Application No. PCT/US2021/037728 International Search Report and Written Opinion dated Oct. 5, 2021, 14 pages.

* cited by examiner

*Primary Examiner* — Eric F Winakur
(74) *Attorney, Agent, or Firm* — Shumaker & Sieffert, P.A.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes a cable to flexible printed circuit board (PCB) connection that provides a reliable connection resistant to flex forces, water ingress and pull forces.

20 Claims, 12 Drawing Sheets

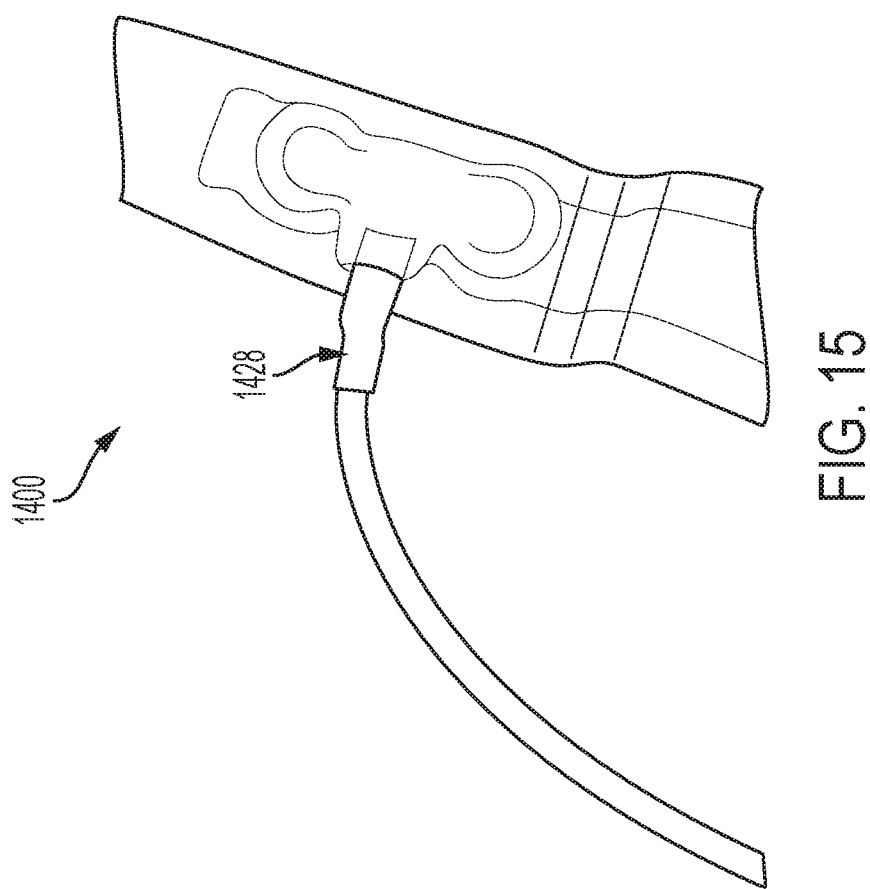

SENSOR JOINT WRAPPING IN A MEDICAL SENSOR

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to sensitivity of the joint connecting the optics and/or flexible printed circuit board (PCB) and the sensor cable, to damage due to flexing back and forth, water ingress and pull forces. Any of these or other forces can cause sensor malfunction or failure, including wire breakage creating an open circuit, wires shorting, etc., which is unacceptable for medical devices.

Accordingly, there is a need in the art for more robust medical sensors that would provide higher reliability and reusability of the sensors.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting diode (LED) communicatively coupled to the communication interface and a detector, communicatively coupled to the communication interface, capable of detecting light. The patient monitoring sensor further includes a cable to optics and/or flexible printed circuit board (PCB) connection that provides a reliable connection resistant to flex forces, water ingress and pull forces. In exemplary aspects, the sensor includes a secure, water resistant sensor cable to flex joint and pull resistance by virtue of a heat shrinkable adhesive joint wrap. In other exemplary aspects, the sensor includes a secure, water resistant sensor cable to flex joint and pull resistance by virtue of an injection molded joint installed over the cable and secured with a base sealing component. In other exemplary aspects, the sensor includes a secure, water resistant sensor cable to flex joint and pull resistance by virtue of an over-molded joint.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. In exemplary aspects, the system includes a sensor with a secure, water resistant sensor cable to flex joint and pull resistance by virtue of a heat shrinkable adhesive joint wrap. In other exemplary aspects, the sensor the system includes a sensor with a secure, water resistant sensor cable to flex joint and pull resistance by virtue of an injection molded joint installed over the cable and secured with a base sealing component. In other exemplary aspects, the system includes a sensor with a secure, water resistant sensor cable to flex joint and pull resistance by virtue of an over-molded joint.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 15 illustrates a top elevation view of a sensor cable with a heat shrinkable joint.

DETAILED DESCRIPTION

Many pulse oximeter sensors utilize a cable connected to a printed circuit board (PCB), which includes a light emitter, such as a light emitting diode (LED) and a photodetector or a cable directly connected to the optics. However, the sensor joint between the cable and the PCB and/or optics is susceptible to damage due to flexing back and forth, water ingress and pull forces.

Accordingly, the present disclosure describes a patient monitoring sensor that includes a secure joint between the cable and the PCB or between the cable and optics. For purposes of this disclosure, further exemplary embodiments describe a cable connection to a PCB or a flex circuit. However, the secure joint described herein is also applicable to a direct cable to optics connection.

In exemplary aspects, the sensor includes a secure, water resistant sensor cable to flex joint, flex resistance and pull resistance by virtue of a heat shrinkable adhesive joint wrap.

In other exemplary aspects, the sensor includes a secure, water resistant sensor cable to flex joint and flex resistance by virtue of an injection molded joint installed over the cable and secured with a base sealing component.

In other exemplary aspects, the sensor includes a secure, water resistant sensor cable to flex joint, flex resistance, and pull resistance by virtue of an over-molded joint.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector capable of detecting light. In exemplary aspects, the system includes a sensor with a secure, water resistant sensor cable to flex joint and pull resistance by virtue of a heat shrinkable adhesive joint wrap. In other exemplary aspects, the sensor the system includes a sensor with a secure, water resistant sensor cable to flex joint and pull resistance by virtue of an injection molded joint installed over the cable and secured with a base sealing component. In other exemplary aspects, the system includes a sensor with a secure, water resistant sensor cable to flex joint, flex resistance and pull resistance by virtue of an over-molded joint.

One or more specific embodiments of the present techniques will be described below. In an effort to provide a concise description of these embodiments, not all features of an actual implementation are described in the specification. It should be appreciated that in the development of any such actual implementation, numerous implementation-specific decisions must be made, which may vary from one implementation to another.

Figure 1:
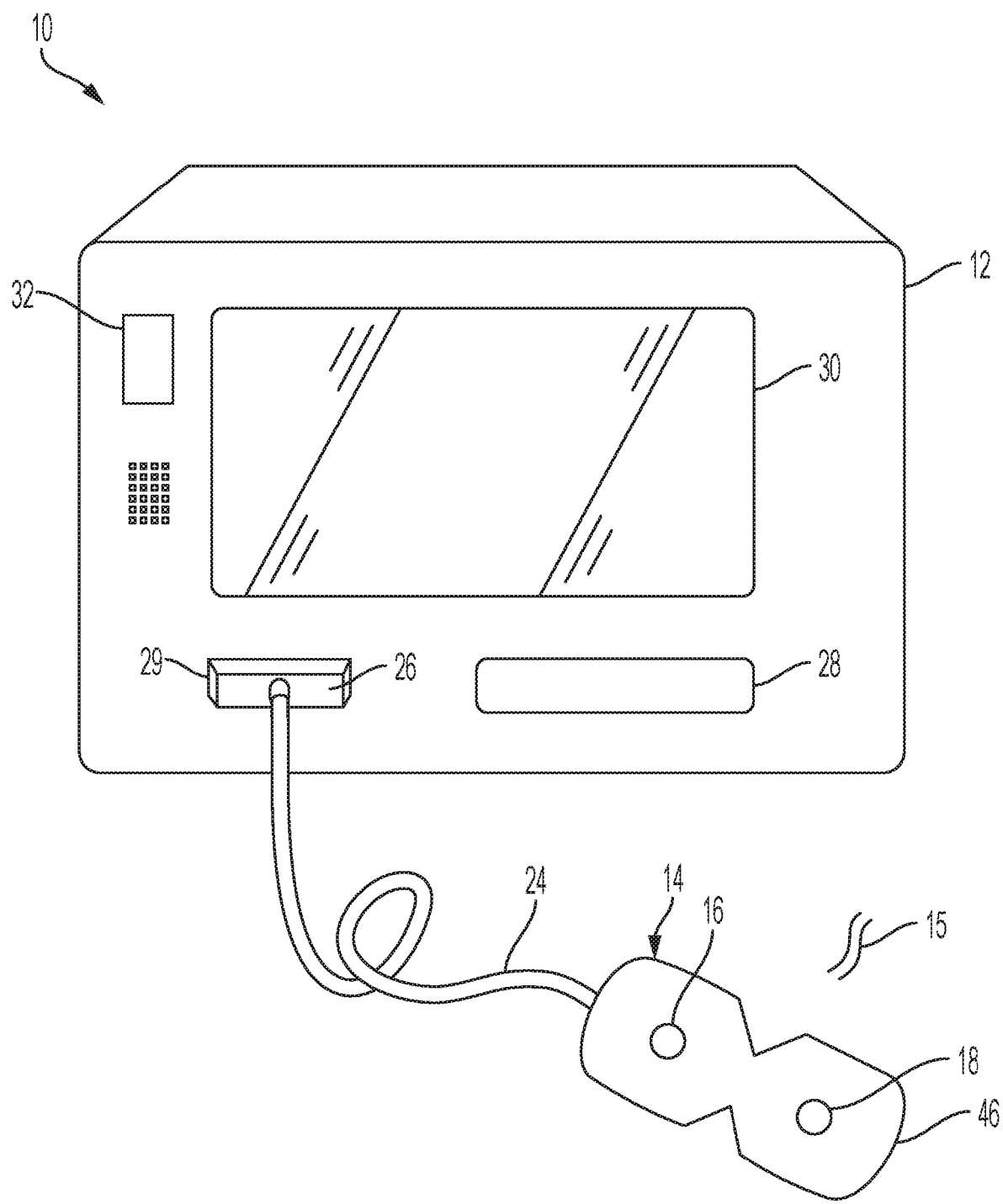
FIG. 1 illustrates a perspective view of an exemplary patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, Colo.), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. The body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner at least partially made from hydrophobic materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
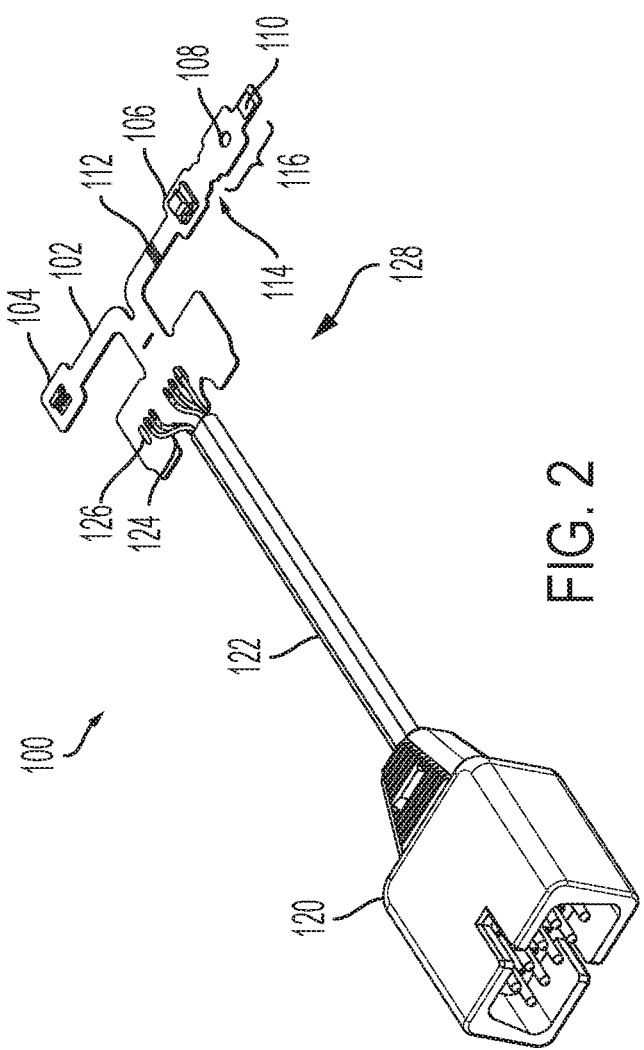
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 and a detector 106 disposed on the body 102 of the sensor 100.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106. In one embodiment, the flap portion 116 includes an adhesive 110 that is used to secure the flap portion 116 to the body 102 after the flap portion 116 is folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

Figure 3:
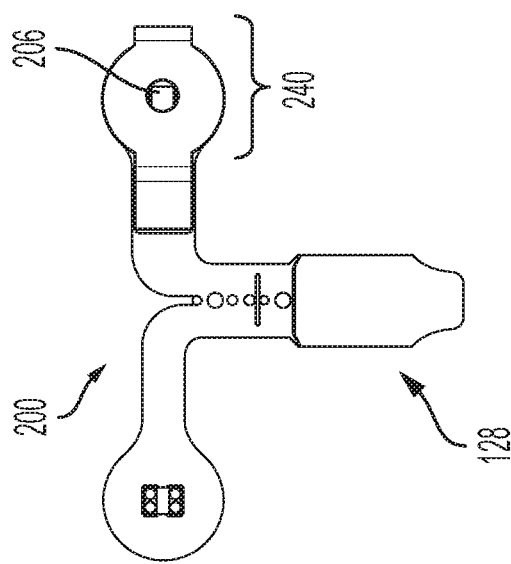
FIG. 3 illustrates a schematic view of an exemplary patient monitoring sensor, in accordance with an embodiment.

Joint section, shown generally at 128, folds together, as shown between FIGS. 2 and 3. An adhesive may be used to secure the joint section together. Further, as will be described in more detail below with reference to FIGS. 6-9, the sensor joint can be additionally secured to provide flex resistance, water resistance and pull resistance.

Referring again to FIG. 2, in exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200.

Further, in exemplary embodiments, at least a portion of the materials used in the construction of the sensor comprise hydrophobic materials, for example including a polyester backing and a silicone patient adhesive. Accordingly, the sensor will absorb less moisture from the environment, for example from a humid environment or from handwashing, etc. This leads to a reduction in the amount of bacteria living within the sensor, enhancing sanitary conditions of the sensor and reducing odor and provides a sensor with more longevity of use and more pleasing effects, and further results in reduction of total cost per patient by extending the useful life of the sensor. Additionally, providing a sensor joint that is water resistant, as will be described in more detail below, further extends the longevity and reliability of the sensor.

Figure 4:
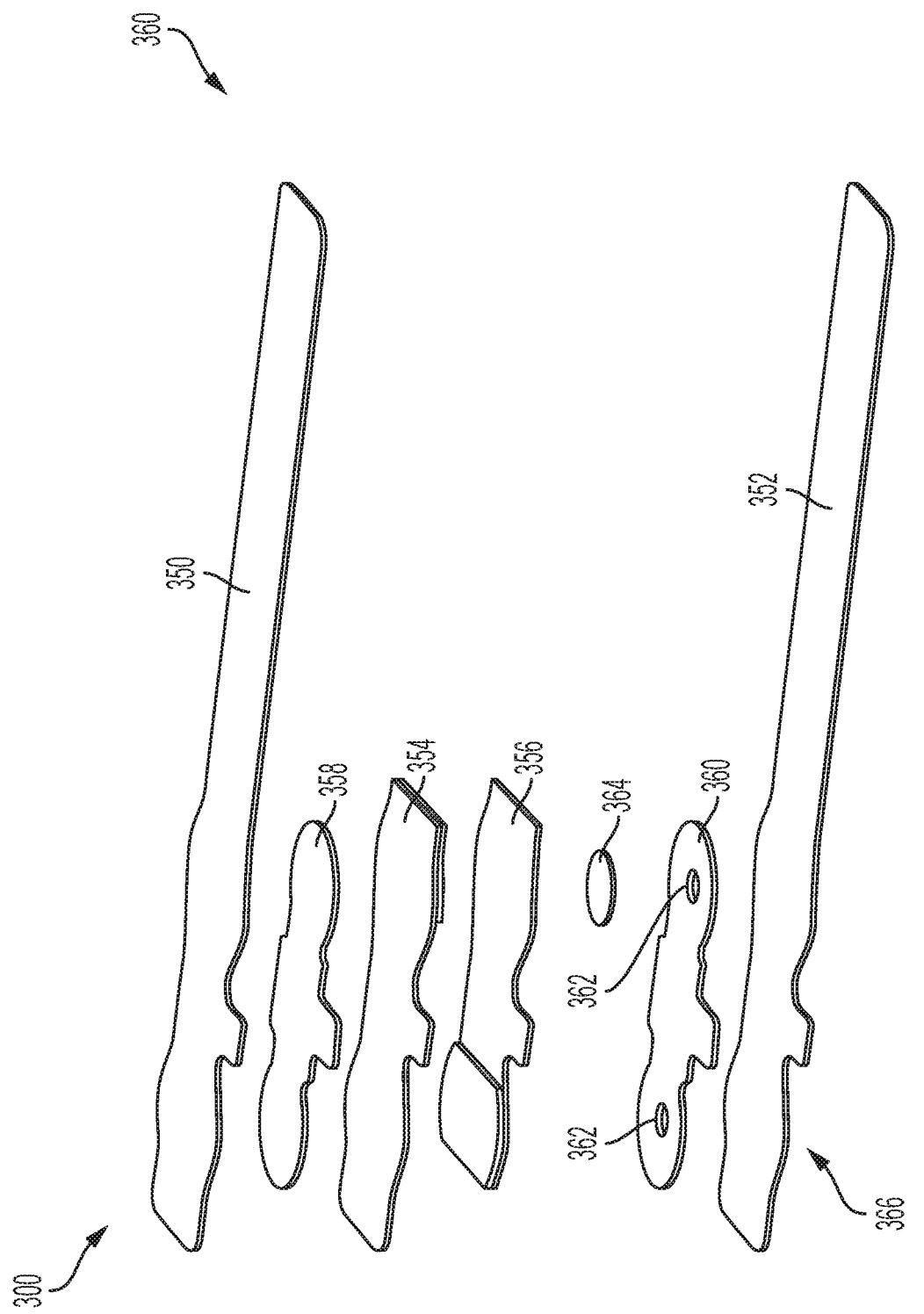
FIG. 4 illustrates a layered schematic view of an exemplary patient monitoring sensor bandage, in accordance with an embodiment.

FIG. 4 illustrates an expanded perspective view generally at 300 of an exemplary layered body/bandage configuration for a pulse oximeter sensor. The configuration includes: an upper bandage 350; an exemplary bottom tape/patient adhesive 352; exemplary top internal liner 354 and bottom internal liner 356, which in exemplary embodiments are discarded during sensor assembly, allowing the bandage to open like a leaflet to insert the flex circuit of FIGS. 2 and 3 into the bandage; a top light blocking layer, for example a metallized tape; a bottom light blocking layer 360, for example a metallized tape with holes 362 configured to allow light to shine through; and a disc 364, comprising for example a polyethylene material, configured to reduce pressure from the LED on the patient. In exemplary embodiments, bottom tape 352 comprises an adhesive layer with a release liner 366 on the patient facing side of tape 352.

Figure 5:
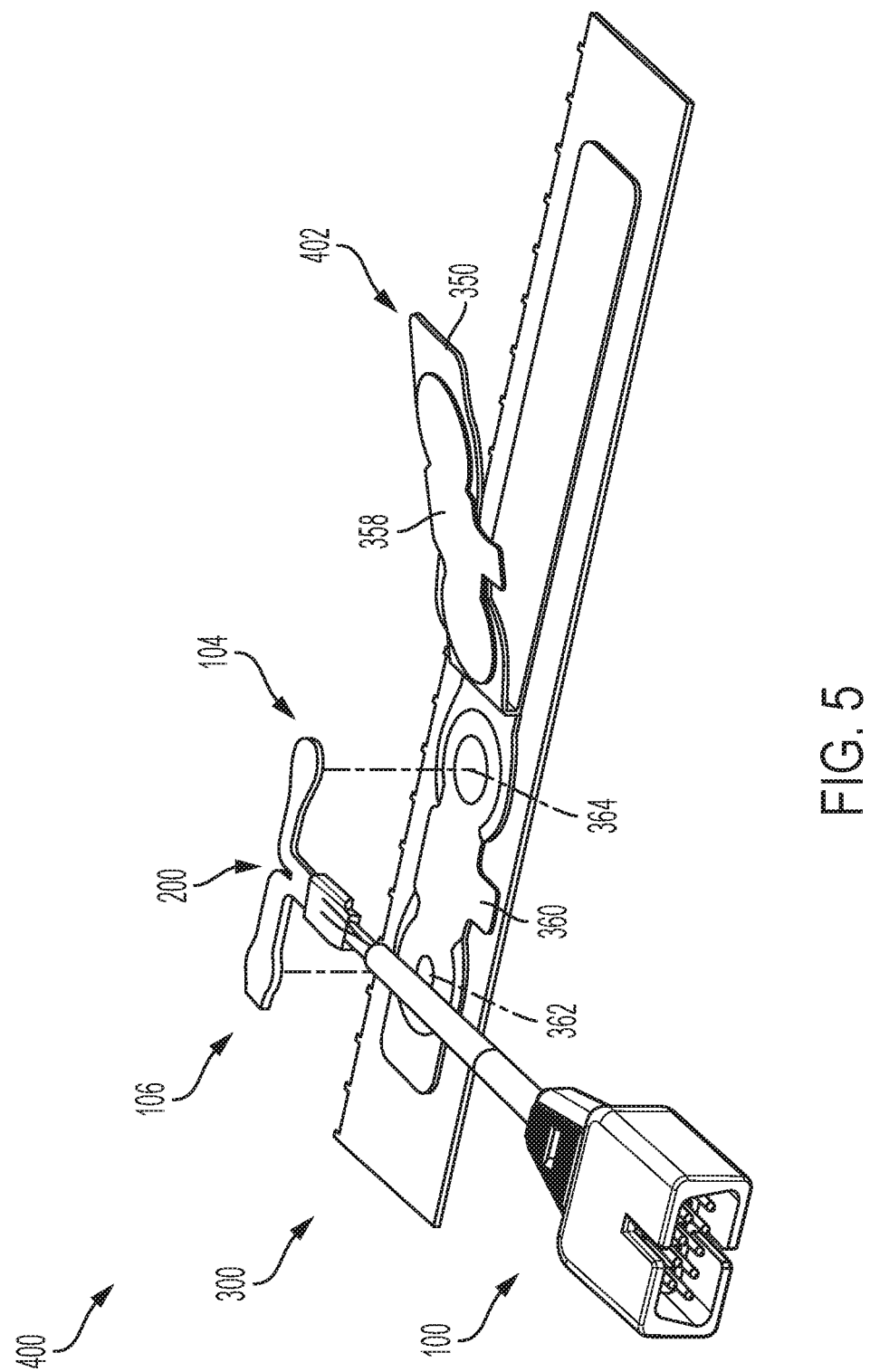
FIG. 5 illustrates a perspective view of an exemplary sensor assembly.

FIG. 5 illustrates a perspective view of exemplary assembly of the flex circuit 200 of FIGS. 2 and 3 into the bandage 300, with internal liners 354, 356 removed to allow positioning of the flex circuit 200 into the bandage, between the light blocking layers 358, 360. As is shown, detector 106 is positioned over hole 362. LED 104 is positioned over disc or ring 364 (which is positioned over another hole 362 (not shown in FIG. 5)). Rapid assembly is facilitated by removable liners 354, 356, as well as the upper bandage 350 and light blocking layer 358 acting as a foldable leaflet 402, the exemplary bandage construction provided as a sub-assembly configured to provide high-volume, fast and repeatable production of sensor assemblies.

Exemplary materials for backing material includes plastics, such as polypropylene (PP), polyester (PES), polyethylene (PE), urethanes, silicone, or the like. Additionally, various layers of the device may be constructed of one or more hydrophobic materials. Bandage, backing and additional possible layers may comprise a variety of thicknesses. Additional embodiments also contemplate thin hydrophobic layers (e.g, 0.1 millimeter polyethylene) inserted in or integral to bandage between the bottom of the sensor bandage and the LED, e.g., to reduce contact pressure on the skin.

Further, exemplary embodiments contemplate select hydrophobic layers or portions of the bandage to prevent absorption of moisture in humid environments, for example on the outside of the bandage, edges of the bandage, etc., or in other locations (including the sensor joint) where bacteria is more likely to come into contact with the bandage, either from humidity from the environment or from washing.

Exemplary materials for patient adhesive include hydrophobic adhesives, such as various silicone adhesives that provide resilience (for re-adhesion) after repositioning, comfort, lack of water loss through patient skin (as measured via trans-epidermal water loss), which lack of water loss correlates with gentle release of the adhesive, etc.

Figure 7:
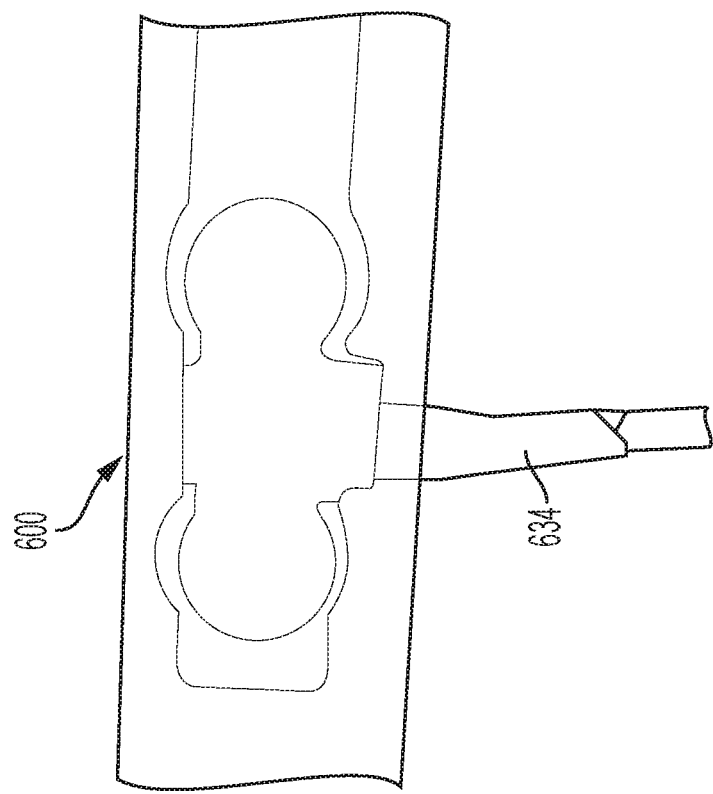
FIG. 7 illustrates a top elevation view of a sensor cable joint with a heat shrinkable adhesive joint wrap and a secondary overwrap.
Figure 6:
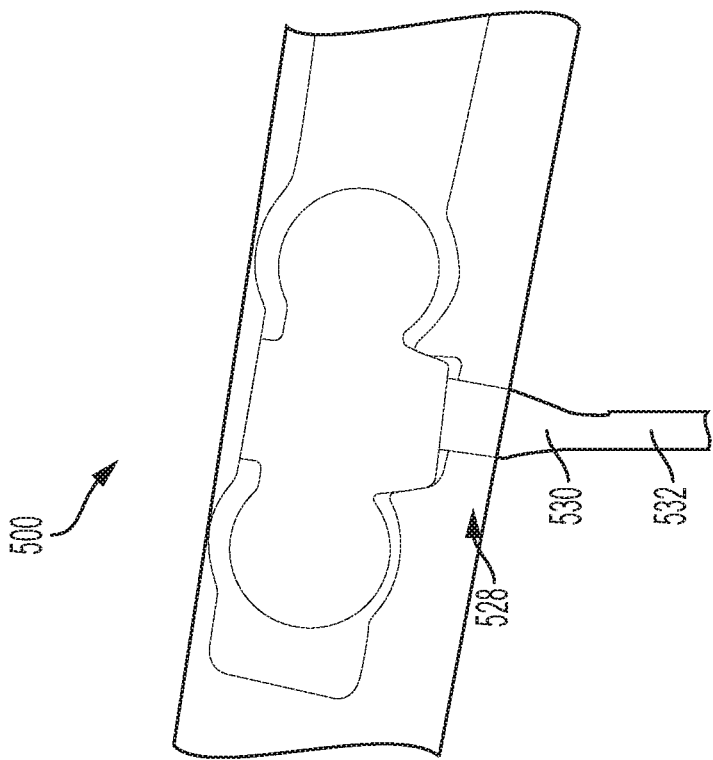
FIG. 6 illustrates a top elevation view of a sensor cable joint with a heat shrinkable adhesive joint wrap.

As we have discussed, the present disclosure describes a patient monitoring sensor that includes a secure joint between the cable and the PCB. In exemplary aspects, the sensor includes a secure, water resistant sensor cable to flex joint and pull resistance by virtue of a heat shrinkable adhesive joint wrap. FIGS. 6-7 illustrate top elevation views of such an exemplary sensor at 500 and 600, respectively, wherein the sensor joint 528 includes an adhesive wrap 530 sealing around the cable 532 to the flexible circuit.

In exemplary embodiments, the adhesive wrap 530 includes materials providing a water resistant joint, e.g., sufficient to pass IPX2 and IPX3 standards. Under such standards, the material for the wrap should be flexible such that it will not un-ravel once wrapped.

In exemplary embodiments, the wrap includes an adhesive layer on the underside that has strong enough adhesion to itself (once wrapped around on itself) to withstand the elastic force to open-up and be flat in relaxed state. Exemplary embodiments provide such flexibility with wrap material that is thin with a low Youngs Modulus of elasticity. This is assisted by the fact that adhesive bonds with high peel force to itself.

Exemplary materials include polypropylene (PP) film adhesive layers that can be heated, causing it to shrink and close gaps or wrinkles created by a wrapping (for example, a hand wrapping) process, providing a watertight seal. FIG. 7 illustrates a top elevation view of an additional, secondary over-wrap 634, providing a more attractive and less wrinkled sensor joint.

FIG. 7 illustrates a water resistant construction that additionally applies a more attractive wrap over top.

FIG. 7 illustrates a woven material substrate. When the adhesive sticks to the woven (not smooth surface) a mechanical interlocking bond is achieved, which is very strong.

Figure 8:
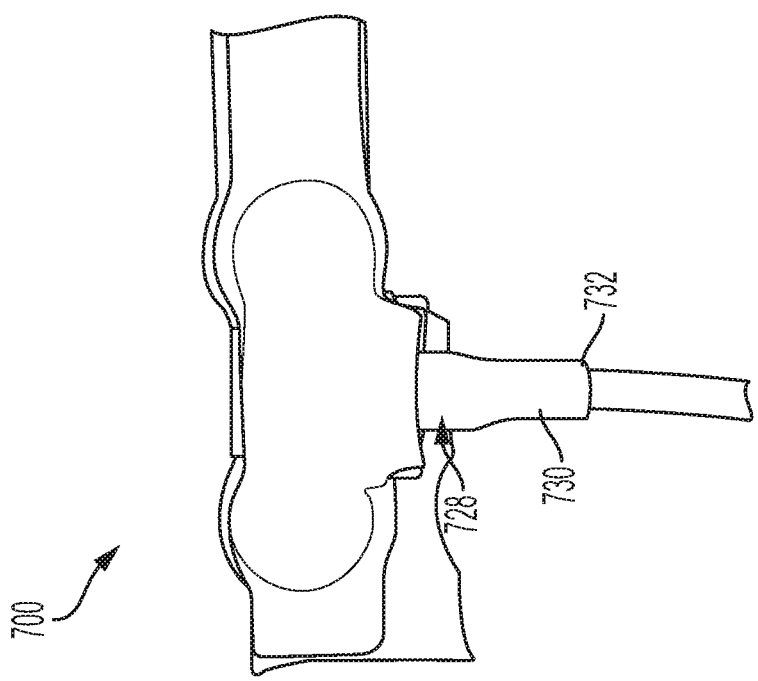
FIG. 8 illustrates a top elevation view of a sensor cable joint with an injection molded joint.

FIG. 8 illustrates a top elevation view of an exemplary sensor 700 that includes a secure, water resistant sensor cable joint 728 with flex and pull resistance by virtue of an injection molded joint 730 installed over the cable and secured with a base sealing component. Injection molded parts can easily be manufactured and hand-assembled by sliding over the cable joint at the time of assembly, allowing for a repeatable joint with strength and good cosmetics. The sealing base component 732 also provides IPX3 water resistance.

Figure 9:
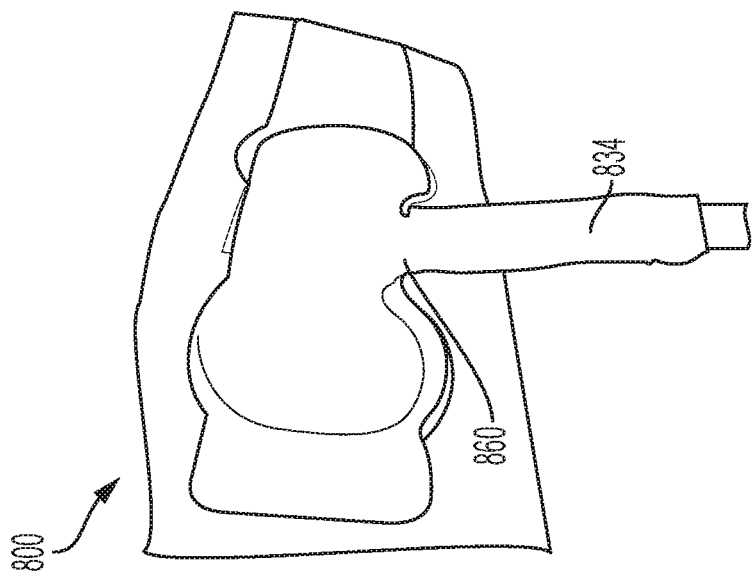
FIG. 9 illustrates a perspective view of a sensor cable joint with a wrap applied over the base of the bandage.

FIG. 9 illustrates a perspective view of a sensor 800 with an exemplary joint covered by a sensor joint wrap 834. In the illustrated exemplary embodiment, the wrap 834 wraps around the injection molded joint, including over the top (trunk) of bandage portion 860 (which is configured to be narrow enough to fit under the wrap), which prevents delamination of the trunk due to lack of forces acting on the bandage.

Figure 10:
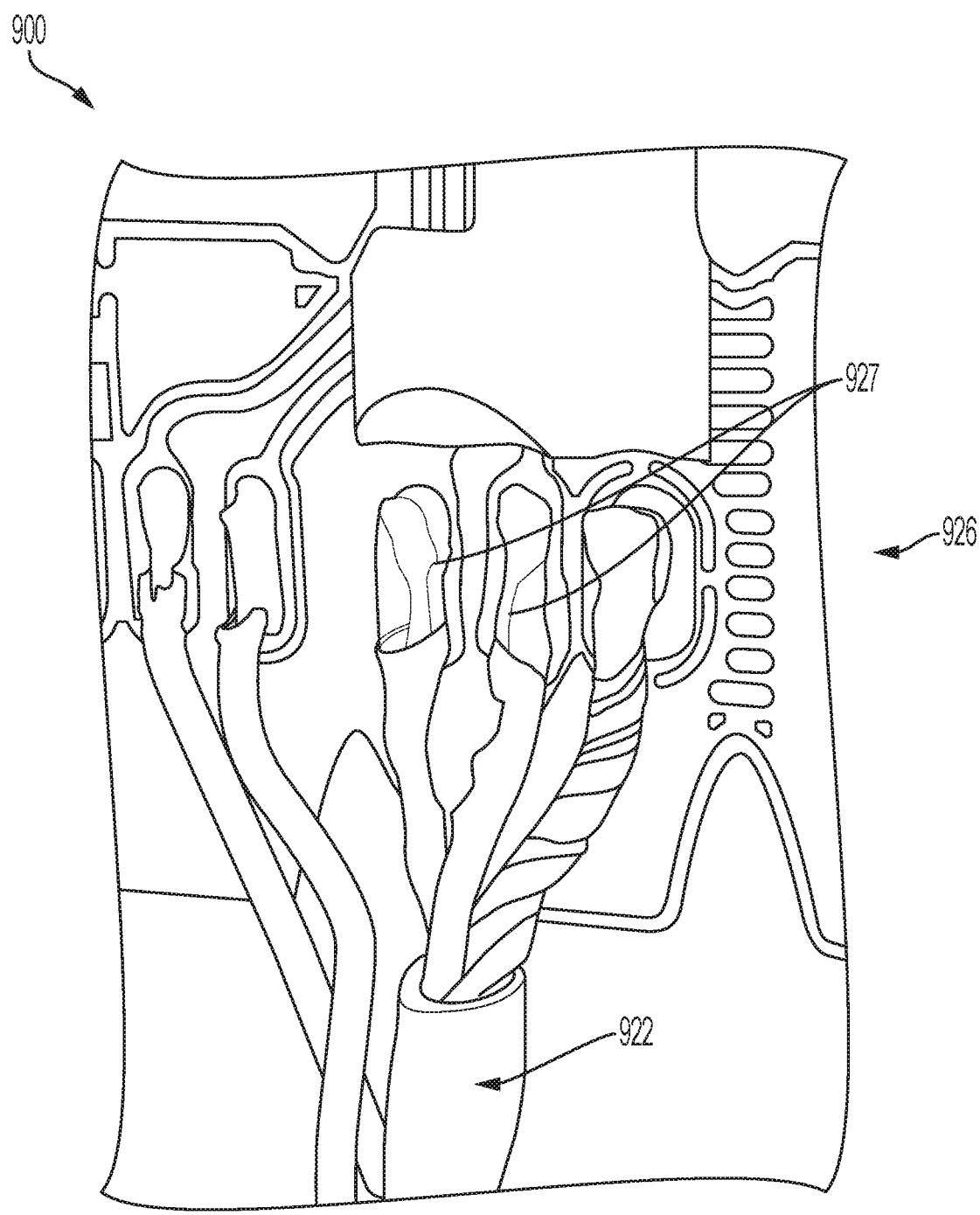
FIG. 10 illustrates a partial front perspective view of a flex circuit having water resistant solder joints.

FIG. 10 illustrates a close-up of an exemplary PCB 900, showing an exemplary cable 922 to PCB connections. Plural solder joints are illustrated generally at 926, with at least one (and in this case two) solder joints covered by a water resistant covering(s) 927, for example an epoxy encapsulate. This PCB covering prevents water from touching the solder joints and causing electrical shorting issues, even if one or more joints or wraps is not completely water resistant. While this exemplary embodiment may be used for any embodiment described herein, it finds particular application with, for example the embodiment of FIG. 9, where a sensor joint over part of the bandage (providing a cleaner, finished look that may not provide as much protection from water ingress).

Figure 11:
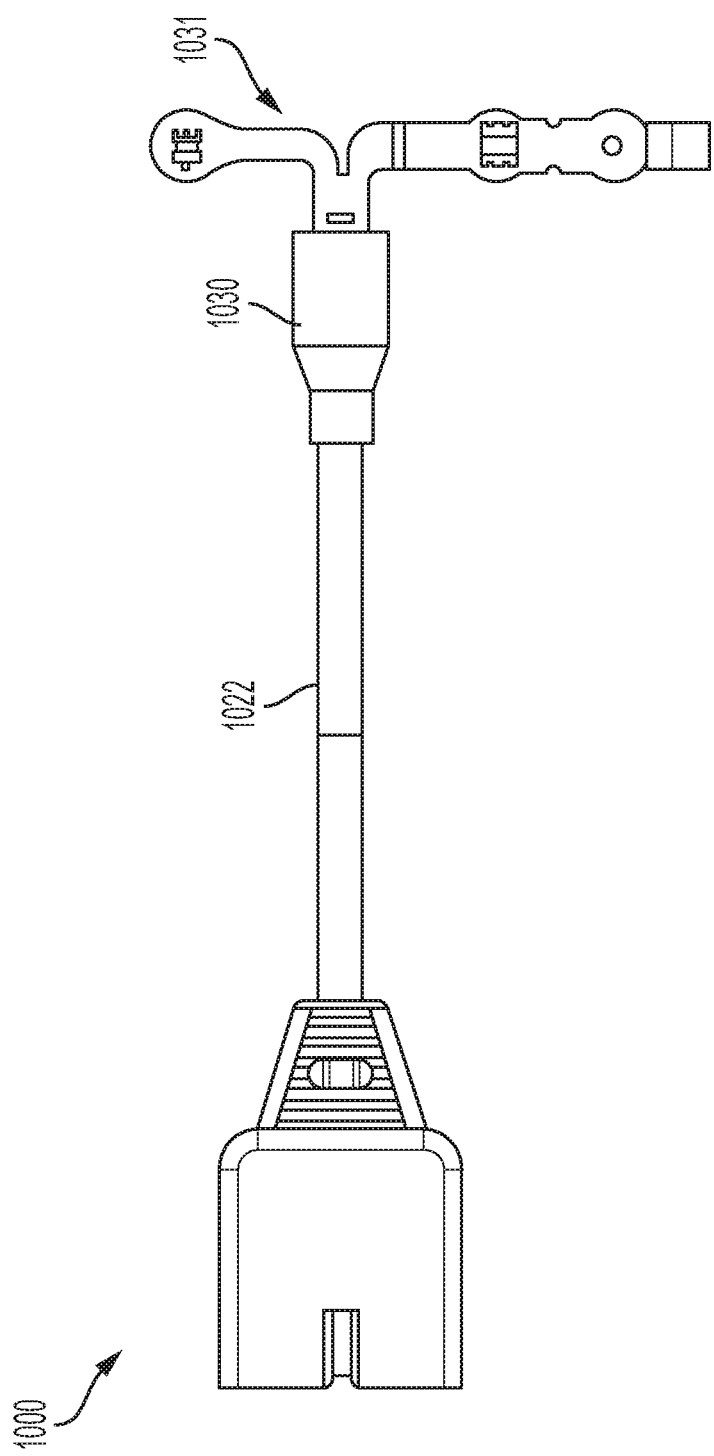
FIG. 11 illustrates a top elevation view of a sensor with a silkscreen line to assist in manufacturing.

FIG. 11 illustrates a top elevation view of an exemplary sensor 1000 having a cable 1022, an injection molded joint 1030 and a silkscreen line or other indicator 1031 on the flex circuit to assist in manufacturing. During manufacturing, indicator 1031 assists the manufacturer by indicating when the edge of the joint sleeve is in the correct position.

Figure 12B:
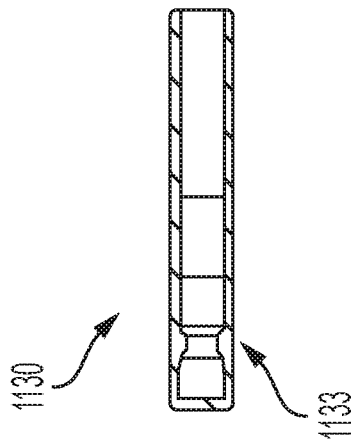
FIG. 12B illustrates a side schematic cross-section view of the injection molded joint covering of FIG. 12A.
Figure 12A:
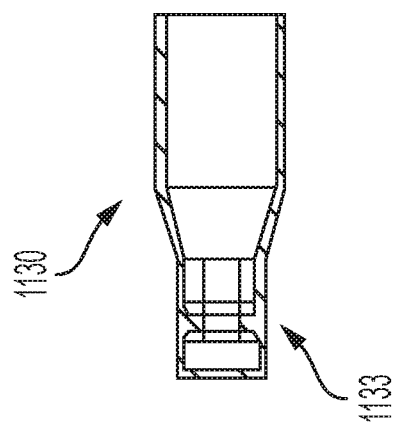
FIG. 12A illustrates a top schematic cross-section view of an injection molded joint covering.

FIGS. 12A and 12B respectively show top and side schematic cross-section views of an exemplary injection molded joint 1130 prior to installation over the cable. The joint includes an interference fit portion 1133, in this case formed as a bump protruding inwardly, interferes with the cable to provide a seal.

Figure 13:
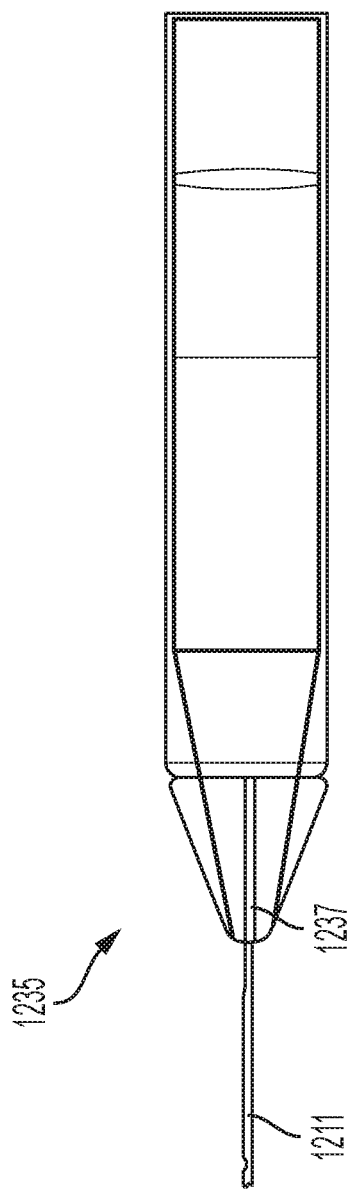
FIG. 13 illustrates a side elevation view of a sensor side injection molded element.

FIG. 13 illustrates another exemplary embodiment including a sensor-side injection molded joint piece, shown generally at 1235, includes an at least one aperture (shown as a slit opening) 1237 configured to slide over the PCB or flex 1211 during assembly. In exemplary embodiments, this slit opening is configured to allow the molded joint piece 1235 to slide it onto a flex from the side.

Injection molded piece 1235 may be provided alone or in addition to a first injection molded piece, such as 1130 in FIGS. 12A and 12B. The profile of the injection molded piece 1235 is configured to provide a gradual decline in profile rather than a steep step-down. The gradual profile advantageously reduces pressure on patient by reducing sharp edges.

Figure 14:
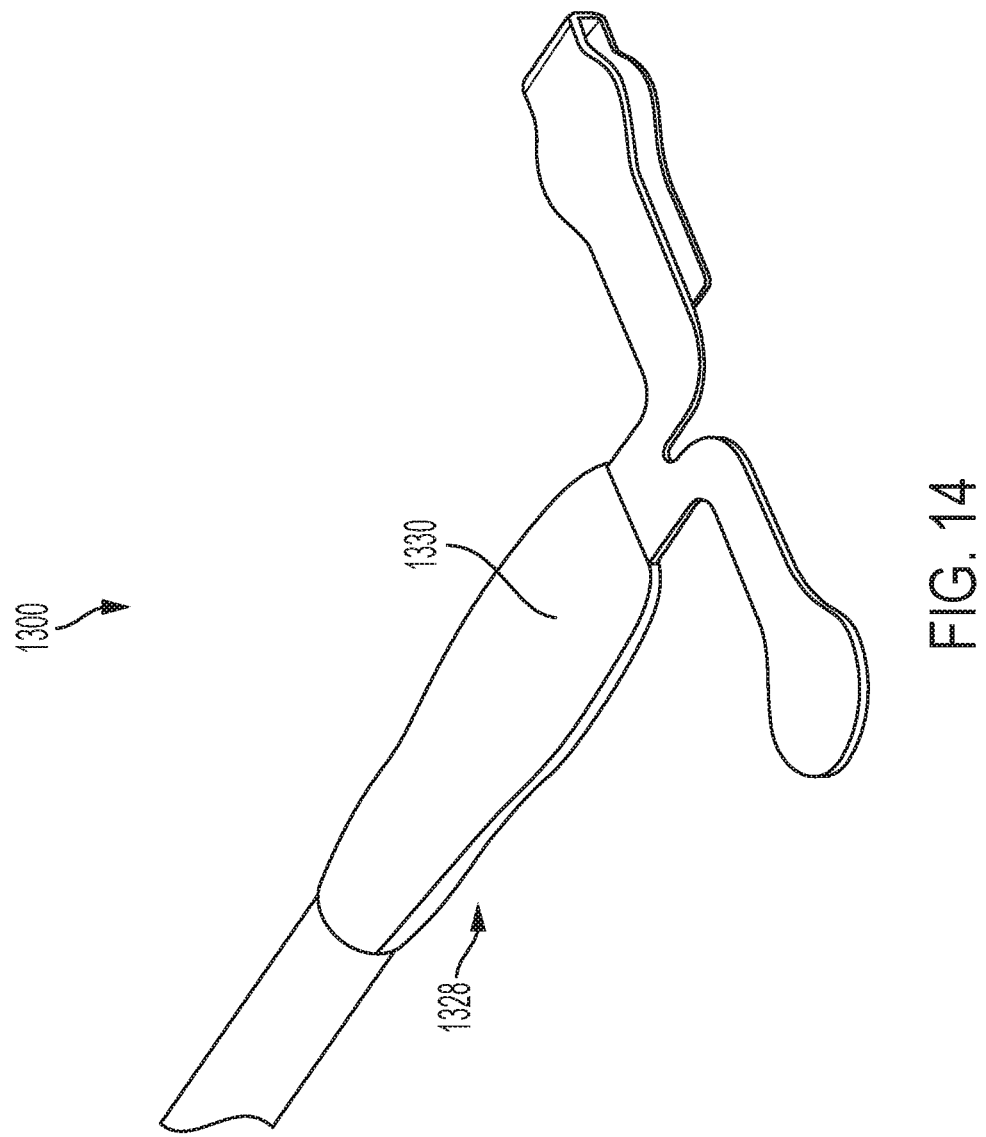
FIG. 14 illustrates a top elevation view of a sensor cable joint with an over-molded joint.

FIG. 14 illustrates a perspective view of an exemplary sensor 1300. In exemplary aspects, the sensor includes a secure, water resistant sensor cable joint 1328 with flex and pull resistance by virtue of an over-molded mechanically interlocked joint 1330. In such a joint, rather than sliding a pre-made part (as in FIG. 12A) over the joint after soldering, joint 1330 is injection molded directly onto the cable joint after the soldering process. This creates a low profile cable joint that is water resistant.

FIG. 15 illustrates a top elevation view of an exemplary sensor 1400. In exemplary aspects, the sensor includes a secure, water resistant cable joint 1428 with flex and pull resistance by virtue of a heat shrinkable wrap that does not include an additional wrap, either under or over the bandage.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising
 a communication interface, through which the patient monitoring sensor can communicate with a monitor;
 a cable communicatively coupled to the communication interface;
 a light-emitting diode (LED) communicatively coupled to the communication interface at least partially via the cable;
 a detector, communicatively coupled to the communication interface at least partially via the cable, capable of detecting light;
 a flexible printed circuit board; and
 a cable to flexible printed circuit board (PCB) joint connection, with wires connected between the cable and flexible printed circuit board, further comprising a supplemental reinforcing material, including an adhesive wrap, an injection molded joint or an overmolded joint, provided around the cable to flexible PCB joint connection, the supplemental reinforcing material comprising resistance to flex forces, water ingress and pull forces, wherein the LED and detector are communicatively coupled to the flexible printed circuit board.

2. The patient monitoring sensor of claim 1, wherein the cable to PCB joint connection comprises an adhesive wrap.

3. The patient monitoring sensor of claim 2, wherein the cable to PCB joint connection comprises a polypropylene (PP), heat shrinkable adhesive wrap.

4. The patient monitoring sensor of claim 3, wherein the cable to PCB joint connection comprises a water resistant, heat shrunk polypropylene wrap.

5. The patient monitoring sensor of claim 4, wherein the cable to PCB joint provides IP33 water resistance.

6. The patient monitoring sensor of claim 5, wherein the cable to PCB joint connection further comprises a secondary over-wrap.

7. The patient monitoring sensor of claim 1, wherein the cable to PCB joint connection comprises an injection molded joint piece positioned over the cable joint.

8. The patient monitoring sensor of claim 7, wherein the cable to PCB joint connection further comprises a water resistant sealed base between the cable and the injection molded joint piece.

9. The patient monitoring sensor of claim 1, wherein the cable to PCB joint connection provides IP33 water resistance.

10. The patient monitoring sensor of claim 1, wherein the cable to PCB joint connection comprises an over-molded joint.

11. A method for making a patient monitoring system, comprising:
 providing a communication interface, through which the patient monitoring sensor can communicate with a monitor;
 providing a cable communicatively coupled to the communication interface;
 coupling a light-emitting diode (LED) communicatively to the communication interface at least partially via the cable;
 coupling a detector capable of detecting light communicatively to the communication interface at least partially via the cable; and
 connecting the cable to a flexible printed circuit board (PCB) at a joint connection, with wires connected between the cable and flexible printed circuit board, wherein the LED and detector are communicatively coupled to the flexible printed circuit board, further comprising applying a supplemental reinforcing material, including an adhesive wrap, an injection molded joint or an overmolded joint, around the cable to flexible PCB joint connection, the supplemental reinforcing material comprising resistance to flex forces, water ingress and pull forces.

12. The method of claim 11, wherein the cable to PCB joint connection comprises an adhesive wrap.

13. The method of claim 12, wherein the cable to PCB joint connection comprises a polypropylene (PP), heat shrinkable adhesive wrap.

14. The method of claim 13, wherein the cable to PCB joint connection comprises a water resistant, heat shrunk polypropylene wrap.

15. The method of claim 14, wherein the cable to PCB joint provides IP33 water resistance.

16. The method of claim 15, wherein the cable to PCB joint connection further comprises a secondary over-wrap.

17. The method of claim 11, wherein the cable to PCB joint connection comprises an injection molded joint piece positioned over the cable joint.

18. The method of claim 17, wherein the cable to PCB joint connection further comprises a water resistant sealed base between the cable and the injection molded joint piece.

19. The method of claim 11, wherein the cable to PCB joint connection provides IP33 water resistance.

20. The method of claim 11, wherein the cable to PCB joint connection comprises an over-molded joint.

\* \* \* \* \*